United States Patent [19]

Krottinger et al.

[11] Patent Number: 4,539,645
[45] Date of Patent: Sep. 3, 1985

[54] AUTOMATED SAMPLE ANALYZER FOR INDUCTION FURNACE ANALYSIS

[75] Inventors: David L. Krottinger; Dale K. Cabbiness, both of Ponca City, Okla.

[73] Assignee: Conoco Inc., Ponca City, Okla.

[21] Appl. No.: 410,721

[22] Filed: Aug. 23, 1982

[51] Int. Cl.³ .................. G05B 11/00; G01N 33/00
[52] U.S. Cl. .................... 364/478; 73/863.01;
  364/499; 364/579; 373/142; 373/157
[58] Field of Search .......... 364/477, 497, 499, 579,
  364/478; 373/118, 138, 142, 157, 140, 146;
  422/63, 64, 65, 78, 67; 73/864.23, 864.81, 863,
  863.01, 863.92, DIG. 9

[56] References Cited

U.S. PATENT DOCUMENTS

| | | | |
|---|---|---|---|
| 3,408,470 | 10/1968 | Grier, Jr. ................. | 373/140 X |
| 3,621,215 | 11/1971 | Netheler et al. ................. | 364/579 |
| 3,985,505 | 10/1976 | Bredeweg ................. | 422/78 X |
| 4,238,450 | 12/1980 | Bredeweg et al. ................. | 422/63 |
| 4,294,126 | 10/1981 | Tomoff et al. ................. | 422/64 X |
| 4,371,971 | 2/1983 | Bredeweg ................. | 373/118 X |
| 4,434,672 | 3/1984 | Williamson et al. ......... | 73/864.23 X |
| 4,462,963 | 7/1984 | O'Brien et al. ................. | 422/63 X |

FOREIGN PATENT DOCUMENTS 0067496 12/1982 European Pat. Off. .......... 497/

Primary Examiner—Felix D. Gruber
Assistant Examiner—Kevin J. Teska
Attorney, Agent, or Firm—Robert M. Hessin

[57] ABSTRACT

An automated sample analyzer for induction furnace analysis includes an induction furnace having an induction coil housing with an induction coil therein. The coil housing has a lower opening through which a crucible with a sample can be moved to allow the sample to be analyzed by burning. An elevator is provided for raising and lowering a crucible to and from the induction coil through the lower opening and includes a cover for covering the lower opening. A rotatable and radially movable tray has crucible openings for holding a series of crucibles. The tray openings also radially receive the elevator allowing the tray to move out of the way of the cover as it moves with the elevator while the elevator holds a crucible. A drive is provided for moving the tray rotationally and radially in a series of steps such that the crucible receptacle openings are sequentially moved to and from the elevator for automated loading and unloading of the crucibles on the elevator. A control coordinates the drive elevator and induction furnace. Recording devices automatically record the analysis.

11 Claims, 11 Drawing Figures

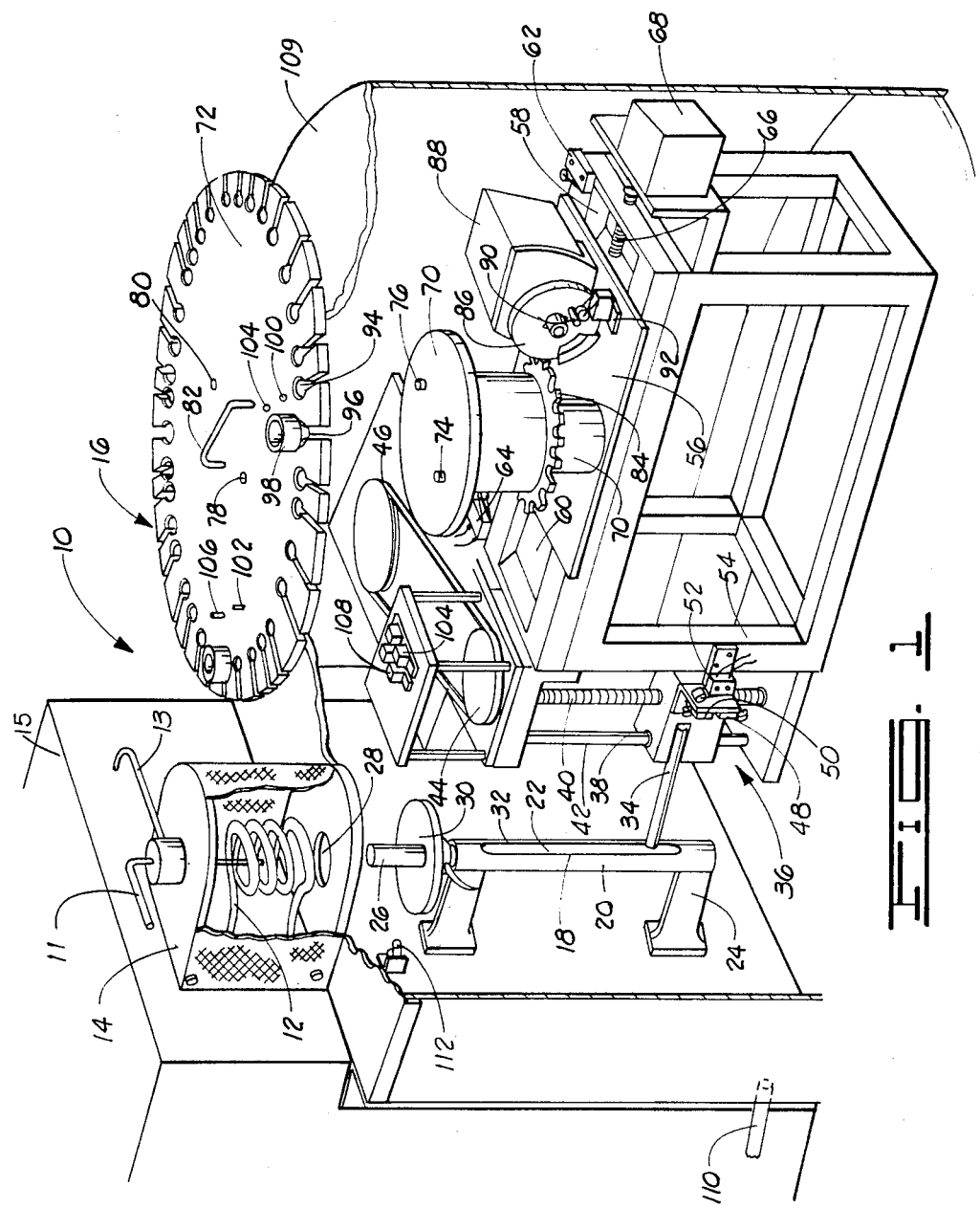

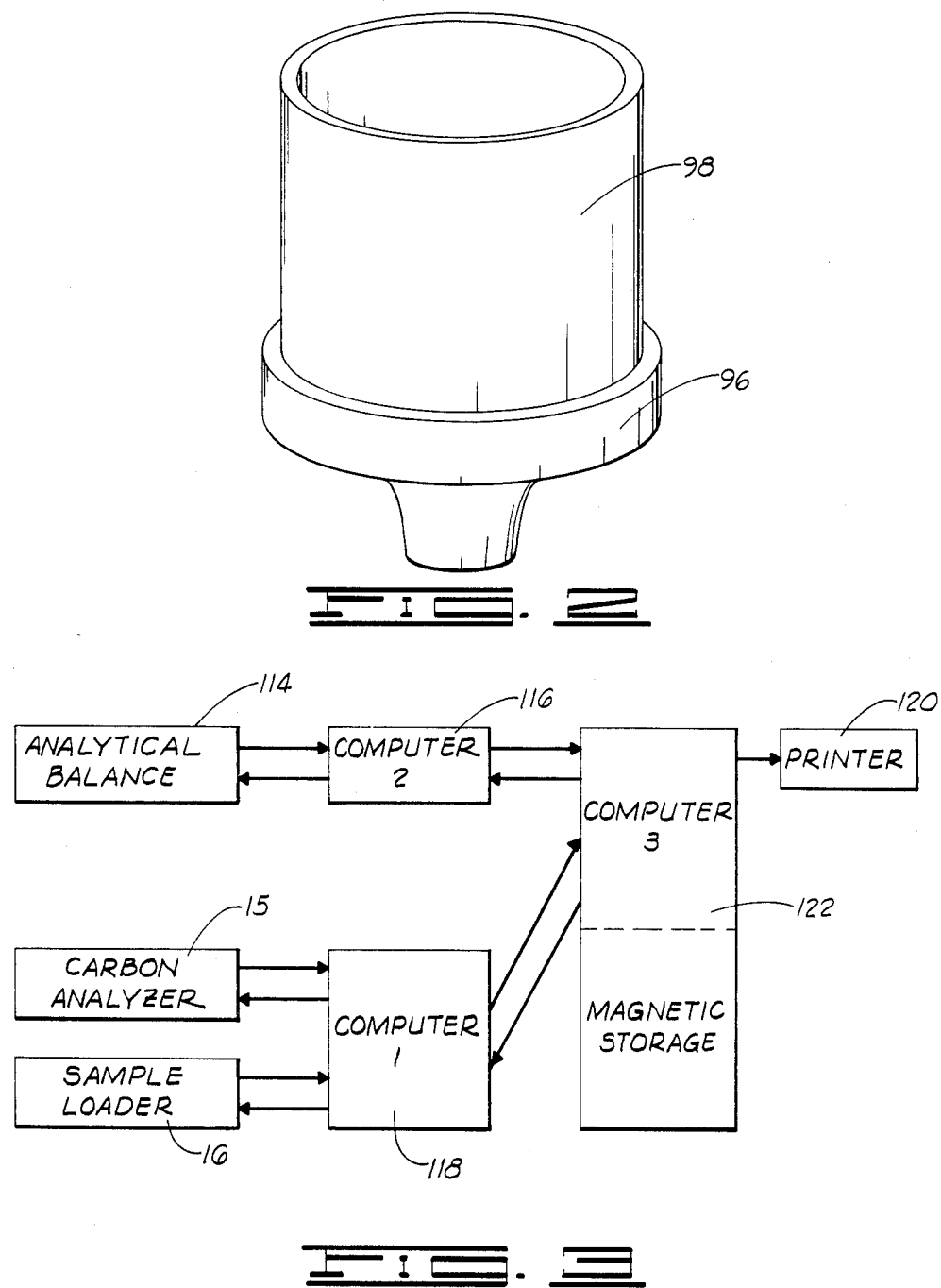

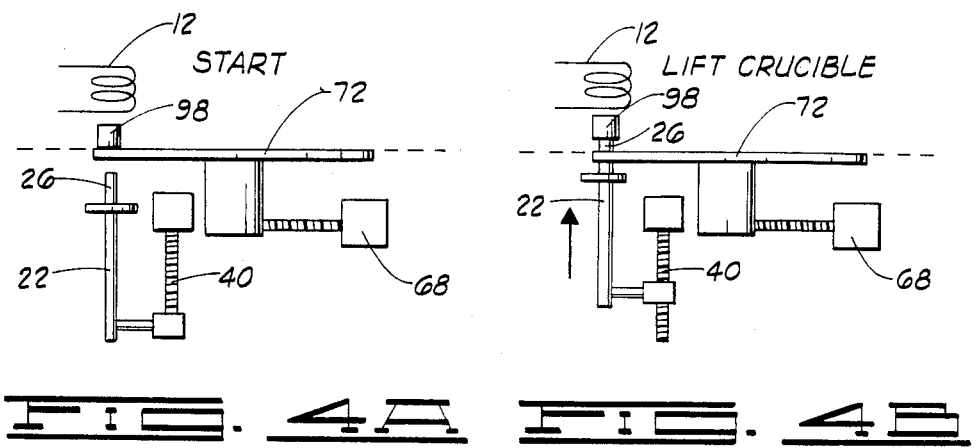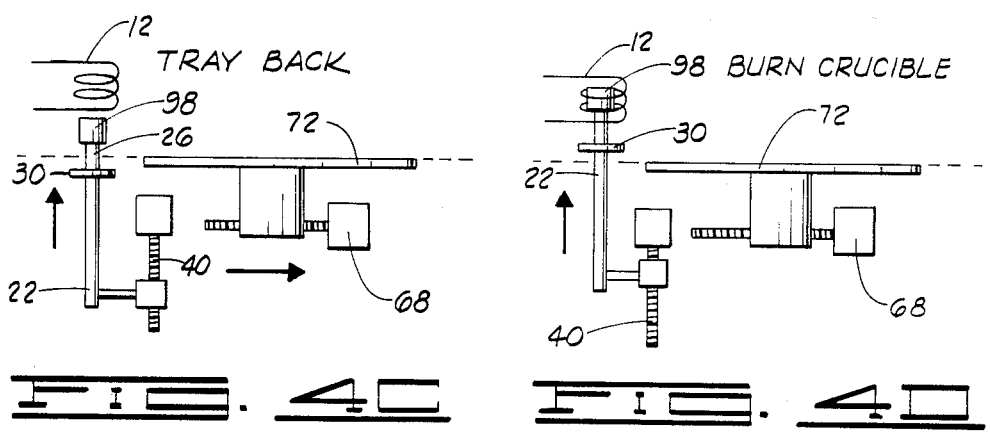

AUTOMATED SAMPLE ANALYZER FOR INDUCTION FURNACE ANALYSIS

BACKGROUND OF THE INVENTION

1. Field of the Invention

This invention relates in general to the devices and methods for automatically and sequentially analyzing multiple samples in an induction furnace. More particularly, but not by way of limitation, it relates to such devices and methods for automated sample preparation, conveying, monitoring and data reporting in analyzing samples in an induction furnace.

2. Description of the Prior Art

There are many different automated delivery systems for use in connection with various type of analyzers in the prior art. Such delivery systems include various means for transferring samples from a sample holding means to an instrument for analysis of samples. Various sample holders, trays for retaining the sample holders, mechanical, hydraulic and electronic moving means, and combinations thereof, have been utilized for transferring samples and containers of samples to and from analysis instruments of various types.

In induction furnace analysis for carbon, a weighed sample is placed in a combustion crucible, ignited by induction in the presence of oxygen in the induction furnace, and the carbon dioxide produced is measured. A disadvantage of the present induction furnace analysis is that the analysis requires many operator steps to perform each sample test. These steps are time consuming and error prone. For example, an operator must place a crucible with a weight sample on a lift assembly, raise the crucible to position in the induction furnace coil, wait for the system to equilibrate, push an analyze button to begin the sample combustion, monitor the instrument during sample combustion to ensure proper operation, read the carbon value from the furnace display, perform calculations and record the results, and then remove and dispose of the empty crucible.

Inasmuch as the induction furnace analysis involves a complex set of procedures and monitoring, the prior art has not discovered any method for automatically performing the induction furnace analysis. One problem particularly related to induction furnaces is that conventional conveyors and delivery systems cannot be connected with or adapted to the raising assemblies which must be utilized in a conventional induction furnace. Another particular problem with the conventional loading of induction furnaces is that the steps of preparing and recording the samples consume all of an operator's time during the analysis process, and, therefore, operators often make mistakes in hurrying to be ready for the next step.

Accordingly, it is an object of this invention to provide an automated induction furnace analysis device which reduces operator interaction with the device and also reduces the likelihood of error in the analysis.

It is another object of the present invention to provide an automated conveyor system to move crucibles to and from an induction furnace analysis position in an induction coil.

Still another object of the present invention is to provide a device for automated sample preparation, conveying and data recording in induction furnace analysis.

SUMMARY OF THE INVENTION

An apparatus for achieving the objects of the present invention has been discovered. The present invention includes an automated device for sequentially transferring crucibles to and from an induction furnace. Typical induction furnaces have an induction coil and a coil enclosure with a lower opening.

The transferring device of the present invention includes a rotatable and radially movable tray disposed adjacent the induction furnace and having a plurality of crucible receptacle openings for receiving crucibles. A tray moving means is provided for radially moving the tray in a series of moving steps such that the tray and a crucible receptacle opening of the tray is alternately radially moved to a position below the lower opening of the coil enclosure and the induction coil and to a position radially away from the lower opening of the coil enclosure and the induction coil. The tray moving means also includes an indexing means for rotationally advancing the crucible receptacle openings one receptacle opening at a time.

The automated transferring device of the present invention also includes a crucible elevator means for raising and lowering a crucible to and from the induction coil through the lower opening of the coil enclosure. This elevator means includes a crucible pedestal extendable through the crucible receptacle opening. The crucible pedestal is provided for lifting and depositing a crucible from and to a crucible receptacle opening in the tray. The crucible elevator means also includes a cover extending beneath the crucible pedestal for covering the lower opening in the coil enclosure.

A control means is provided for controlling the tray moving means and the crucible elevator means to cooperatively raise and lower crucibles to and from the induction coil and from and to sequential receptacle openings.

The present invention also provides an automated induction furnace analysis device by combining the automated device for sequentially transferring crucibles with a weight reading means, a combustion chemical reading means and a computing means. The weight reading means detects the weight of a sample placed in a crucible and indicates weight data from this detection. The combustion chemical reading means detects combustion chemicals in the coil enclosure and indicates combustion chemical data from this detection. The computing means is connected for receiving this data and computes and records, sequentially, a compared analysis of this data responsive to the control means of the device which sequentially transfers the crucibles to and from the induction furnace. In this manner, a completely automated operation of sequential induction furnace analysis can be achieved without operator attendance.

For a further understanding of the invention and further objects, features and advantages thereof, reference may now be had to the following description taken in conjunction with the accompanying drawings.

BRIEF DESCRIPTION OF THE DRAWINGS

FIG. 1 is a perspective view of the furnace and automatic transferring device of the present invention.

FIG. 2 is a perspective view of a ceramic crucible holder and crucible shown in FIG. 1.

FIG. 3 is a schematic view of the automated furnace analysis device of the present invention.

FIGS. 4A through 4H are schematic views of the operation sequence of the transferring device of the present invention.

DESCRIPTION OF PREFERRED EMBODIMENTS

Figure 4E:
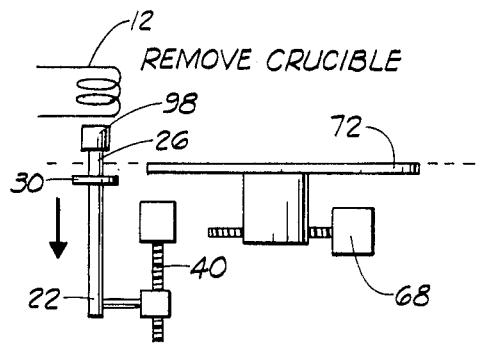

Referring now to FIG. 1, an induction furnace is shown generally at 10. The induction furnace 10 is of a conventional type and includes an induction coil 12 and a coil housing or enclosure 14. An oxygen supply tube 11 extends through the top of enclosure 14 into the coil 12. An exhaust gas tube 13 extends from the top of enclosure 14 into a conventional analyzer device 15. Analyzer 15 measures the combustion product (carbon dioxide) which is produced when a sample is positioned within the coil 12 and the coil 12 is activated to burn the sample. An example of a typical induction furnace analyzer 15 is Model No. WR-12 constructed by Laboratory Equipment Corporation of St. Joseph, Mich. and a similar model constructed by Wilkens-Anderson Company of Chicago, Ill.

Attached to the induction furnace analyzer 10 is an automated crucible transferring device 16. The automated transferring device 16 operates to load and unload, sequentially, a series of crucibles to the induction furnace 10.

Attached to the side of furnace 10 is a crucible elevator 18. The elevator 18 includes a slotted lift cylinder 20 which contains a lift shaft 22. The slotted lift cylinder 20 is connected to the side of furnace 10 by a pair of lift cylinder mounts 24.

The upper end of lift shaft 22 extends out of the slotted lift cylinder 20. Attached to this upper end of lift shaft 22 is supported pedestal 26. The support pedestal 26 is adapted to extend through a lower opening 28 in housing 14 to carry a sample into position in coil 12. Surrounding the upper end of lift shaft 22 just below pedestal 26 is a cover flange 30. When support pedestal 26 is supporting a sample in position in coil 12, the cover flange 30 covers the lower opening 28 completely enclosing the sample so as to contain the combustion gases inside housing 14.

Extending through the slot 32 in the slotted lift cylinder 20 is a connector rod 34. The connector rod 34 extends from lift shaft 22 to an elevator drive mechanism 36. By this connection lift shaft 22, cover flange 30, and support pedestal 26 all move vertically in response to the movement of the elevator drive mechanism 36.

The elevator drive mechanism 36 includes a lift block 38, a drive screw 40, a pair of drive sprockets 44 connected by a drive belt 46 and a drive motor (not shown). A guide shaft 42 extends vertically through lift block 38 to guide its vertical movement. As drive screw 40 rotates the lift block 38 is raised and lowered. The upper end of drive screw 40 is connected by drive sprockets 44 and drive belt 46 to a motor. Through directional operation of the motor the drive screw 40 rotates to raise and lower lift block 38. By means of connector rod 34 lift shaft 22 is raised and lowered in slotted lift cylinder 20 responsive to the movement of lift block 38.

A lower limit switch 48 is attached to lift block 38 to indicate (and signal) when lift block 38 reaches the bottom of its travel on drive screw 40. An upper limit switch 50 is attached to lift block 38 to indicate the upper limit of the lift block travel on drive screw 40. A switch 52 is attached to a frame 54 to indicate when lift block 38 is in an intermediate position. Switches 48, 50 and 52 are connected through a control means to the drive motor to allow the drive motor to stop the lifting of lift shaft 22 at its lower, upper and intermediate ranges.

Attached to the upper side of frame 54 is a table 56. Table 56 is connected by means of a dovetail slide 58 in a slot 60 which extends across the upper side of frame 54. In this manner, table 56 slides horizontally toward and away from the furnace analyzer 10 and elevator 18.

A rear limit switch 62 is mounted on frame 54 to indicate the limit of travel of table 56 in slot 60 away from furnace analyzer 10. A front limit switch 64 indicates the limit of travel of table 56 within slot 60 toward furnace analyzer 10.

A drive screw 66 is threaded into table 56 and connected to a motor 68. Operation of the motor 68 turns drive screw 66 and, according to the direction of rotation of screw 66, moves table 56 toward or away from furnace analyzer 10.

Rotationally mounted on top of table 56 is a tray support cylinder 70. This tray support cylinder 70 supports a tray 72. Tray 72 rests upon tray support cylinder 70 and is retained in connection therewith by pins 74 and 76 which extend upwardly from tray support cylinder 70 through holes 78 and 80 in tray 72. A handle 82 connected to the central portion of tray 72 allows tray 72 to be lifted from its position on tray support cylinder 70.

Extending about the tray support cylinder 70 is a cam follower sprocket 84. A vertically disposed index cam disk 86 is rotationally mounted to a motor shaft and motor 88 such that the index cam disk 86 mates with cam follower sprocket 84. As motor 88 rotates index cam disk 86 one revolution a sprocket tooth of cam follower 84 is advanced. A pin 90 extends from the side of index cam disk 86 and cooperates with a limit switch 92 mounted on table 56 to indicate when the index cam disk has completed one revolution. Motor 88 is mounted on table 56.

At uniformly spaced distances about the periphery of tray 72 are a plurality of slotted holes 94. These slotted holes 94 are specifically sized for receiving ceramic crucible holders 96. The crucible holder 96 receives in its saucer like upper surface crucibles 98. The slotted holes 94 are sized so that support pedestal 26 can extend therethrough and raise the ceramic crucible holder 96 and a crucible 98 from the tray 62. The slotted holes 94 have a slotted portion which extends through the periphery of the tray 72. This slotted portion is sufficiently large to allow the tray 72 to be withdrawn away from support pedestal 26 while support pedestal 26 is supporting a crucible above tray 72 through the hole 94.

As shown in FIG. 2, the ceramic crucible 98 can be supported by a crucible holder 96. Although not necessary in many instances the holder 96 can help to retain the crucible in proper position for raising and lowering to and from the tray 72.

Referring now to FIGS. 4A through 4H the operational sequence for sequentially loading and unloading crucibles to and from the induction coil 12 and from and to the sequential spaces of the tray 72 is shown.

As shown in FIG. 4A, tray 72 is first positioned so that a selected slotted hole extends over support pedestal 26. Motor 68 has moved the table 56 to the forward limit of its travel. Lift shaft 22 is at the lower end of its travel.

As shown in FIG. 4B, the first step in the operational sequence is to rotate drive screw 40 so that lift shaft 22 is raised. The lift shaft 22 raises pedestal 26 until it supports a ceramic crucible holder 96 and its crucible 98 above and disengaged from its slotted hole 94 in tray 72. When the lift block 38 encounters limit switch 52 the raising of lift shaft 22 is halted. This prevents cover flange 30 from encountering tray 72.

As shown in FIG. 4C, the activation of limit switch 52 also causes motor 68 to drive table 56 and tray 72 radially away from furnace analyzer 10. When the table 56 encounters rear limit switch 62 the operation of motor 68 is halted.

As shown in FIG. 4D after table 56 reaches its rear limit switch drive screw 40 is again activated to raise lift shaft 22. When the lift block 38 reaches the top of its travel the crucible 98 is positioned inside coil 12 and cover flange 30 covers the opening 28 in housing 14. When the limit switch 50 is activated the rotation of screw 40 to raise lift shaft 22 is halted.

Figure 4F:
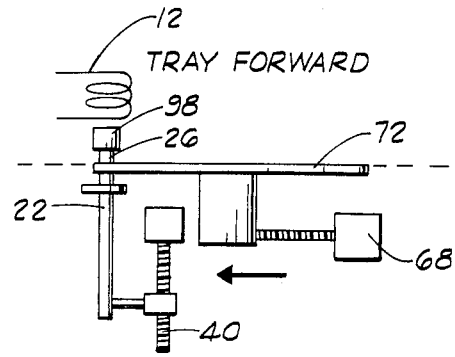

At this point, the crucibles and its sample are in position for coil 12 to be activated. The activation of upper limit switch 50 begins the analyze sequence on the furnace analyzer. This sequence continues until the burn is completed and a chemical analysis is indicated on the amount of carbon dioxide produced in the burner. When the burn and the analysis are completed the motor driving shaft 40 is actuated so that lift shaft 22 moves downwardly until lift block 38 encounters switch 52. At this point the movement of the lift shaft 22 is halted. Actuation of the switch 52 then causes motor 68 to be activated to move table 56 and tray 72 forward. This is shown in FIG. 4F. The tray moves forward until it reaches a position such that the slotted hole from which the crucible was removed is below the crucible again.

Figure 4G:
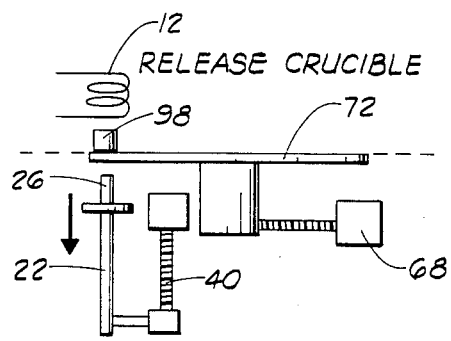
Figure 4H:
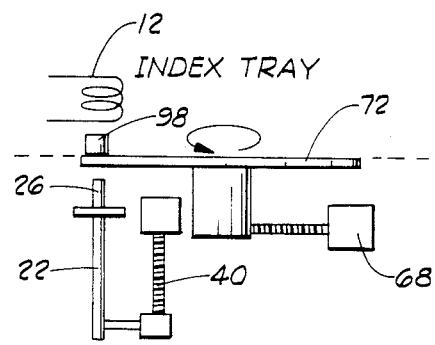

As shown in FIG. 4G, the activation of front limit switch 64 causes lift shaft 22 to again move downwardly. This causes crucible 98 to be deposited in its position in its original slotted hole 94. When the lift block 38 reaches the lower end of its travel it activates lower limit switch 48 which causes the motor 88 to index tray 72. Tray 72 is thus moved such that the next slot and the next crucible are in position as shown in FIG. 4A.

In order to provide an indication of the first and last crucible in a series of crucibles to be analyzed as described above, two sets of holes are provided in tray 72. The first set of holes is an outer set of holes 100. The outer set of holes 100 consists of a set of holes just inward from each slotted hole 94. By placing a pin 102 through a selected one of the first set of holes adjacent a last crucible, the position of the last crucible in a series of samples is indicated. A switch 104 is provided just beneath tray 72 and is encountered by pin 102 when tray 72 reaches this limit.

The second set of holes 104 are provided just inside the first set of holes 100. As with pin 102 a pin 106 extending through a selected one of the holes 104 indicates the position of the first crucible in a series of samples. A switch 108 is provided adjacent switch 104 such that it will be activated by pin 106 when the tray is located in a first sample position.

To provide completely automated operation of the system an electronic analytical balance 114 (FIG. 3) with digital output such as the Sartorius Model 1201 top loading balance is used for sample weighing. By utilizing this balance in connection with a computer 116 (microprocessor based controlling device such as Rockwell AIM 65) the sample weight can be directly associated and recorded with a particular position on tray 72. In this way, as the samples are weighed and placed on the tray 72 the weight is recorded and saved in the file position according to the slotted hole in tray 72.

A computer 118 can also receive digital information from the carbon analyzer 10. By specifically allocating a carbon dioxide amount data file for each slotted hole in tray 72 the data from furnace analyzer 10 can be combined with the weight data received from the electronic balance. This can be achieved by means of coordinating and controlling the sample loader 16 with computer 118. In this manner, as each sample is advanced by the sample loader and the furnace analyzer receives data the microprocessor can process this information to indicate the carbon value in the sample. This information can be recorded on a suitable medium for later reading by an operator, or printing on a printer 120. A third computer 122 with magnetic storage can be connected to the first two computer 116 and 118 for this purpose and to coordinate the process.

In the analysis for organic carbon the sample treatment step would normally result in a large amount of moisture being absorbed from the surrounding air. This is because the sample must remain exposed while it is waiting to be tested. The excess moisture in the sample often causes splattering of the sample during the burn and incomplete combustion. The present invention avoids this problem by enclosing the sample tray and its loading mechanism inside an aluminum box 109. Dry air or nitrogen is continuously circulated through the box through an inlet 110 in the side of the box. This box also serves to contain any hot crucibles that could drop from the pedestal.

It is desirable to utilize a specific detector to determine if a crucible gets stuck in the combustion chamber and remains there after the pedestal is lowered. This can be achieved by locating an infrared photo detector 112 (including an emitter and a detector) beneath housing 14 adjacent lower opening 28. As the crucible is lowered its heat will be detected by the infrared detector and it can be determined that the crucible did not stick in the combustion chamber.

If the infrared detector indicates that a crucible is stuck in the combustion chamber the detector can signal the microprocessor control to stop the operation of the sample loader and activate a warning signal.

Thus, the automatic sample analyzer of the present invention is well-adapted to attain the object and advantages mentioned as well as those inherent herein. While presently preferred embodiments of the invention have been described for the purpose of this disclosure, numerous changes in the construction and arrangement of parts can be made by those skilled in the art which changes are encompassed within the spirit of this invention as defined by the appended claims.

The foregoing disclosure and the showings made in the drawings are merely illustrative of the principles of this invention and are not to be interpreted in a limiting sense.

What is claimed is:

1. An automated sample analyzer for induction furnace analysis comprising:
    an induction furnace having an induction coil housing with a lower opening and an induction coil located therein to and from which a crucible with a sample therein can be moved through said lower opening;
    elevator means for raising and lowering a crucible to and from said induction coil through said lower opening, including a crucible pedestal and a cover extending beneath said crucible pedestal for covering said lower opening;

a rotatable and radially movable tray disposed adjacent to said elevator means and having a plurality of crucible recetacle openings for receiving and holding crucibles and radially receiving said crucible pedestal;

tray moving means for rotationally and radially moving said tray in a series of steps such that said crucible receptacle openings are sequentially moved to and from said crucible pedestal for sequential loading and unloading of crucibles on said crucible pedestal, said tray moving means including a radial moving means for alternately radially moving a selected one of said crucible receptacle openings in said tray to said crucible pedestal and beneath said lower opening and radially moving said tray away from said crucible pedestal and said lower opening, said tray moving means also including an indexing means, for rotationally advancing said crucible receptacle openings one receptacle opening at a time; and control means for controlling said tray moving means, said elevator means and said induction furnace to sequentially and cooperatively raise and lower crucibles to and from said crucible receptacle openings in said tray, raise and lower crucibles to and from the said induction coil and analyze by induction furnace analysis samples in said crucibles when disposed in said induction coil.

2. The automated sample analyzer of claim 1 which further comprises:

weight reading means for detecting weight data of a sample in a crucible;

combustion chemical reading means for detecting combustion chemical data from induction furnace analysis in said induction furnace; and recording and computing means connected to said weight reading means, said combustion chemical reading means, and said control means for receiving data therefrom and recording and computing a compared analysis of this data responsive to said control means such that a compared analysis is recorded for each sample in each crucible sequentially moved to and from said induction coil.

3. The automated sample analyzer of claim 2, which further comprises:

an infrared detector disposed adjacent to said elevator means for detecting the presence and absence of crucibles on said crucible pedestal as said crucible pedestal is raised to said induction coil and lowered from said induction coil; and wherein said control means is connected to said infrared detector for halting operation of said sample analyzer when a crucible becomes
stuck in said induction coil housing.

4. The automated sample analyzer of claim 1 wherein said tray includes an indication means for indicating the location of a last crucible in a series of crucibles disposed in said crucible receptacle openings and wherein said control means is connected to said indication means such that said control means halts the operation of said sample analyzer responsive to said indication means.

5. The device of claim 1 which further comprises:
an enclosure extending about said elevator means, said tray and said tray moving means for protecting samples disposed on said tray; and gas supply means connected to said enclosure for filling said enclosure with a gas not reactive with samples disposed on said tray.

6. The device of claim 1 wherein said tray moving means comprises:

a frame disposed adjacent to said elevator means;

a table movably mounted on said frame for horizontal movement toward and away from said elevator means;

a spindle rotatably mounted on said table and upon which said tray is received, such that said tray is disposed horizontally and rotates with said spindle;

screw drive means mounted on said frame and connected to said table for horizontally moving said table toward and away from said elevator means; and cam drive means mounted on said table and connected to said spindle for rotationally advancing said crucible receptacle openings one receptacle opening at a time.

7. An automated sample analyzer for induction furnace analysis comprising:

an induction furnace having an induction coil housing with a lower opening and an induction coil located therein to and from which a crucible with a sample therein can be moved through said lower opening;

elevator means for raising and lowering a crucible to and from said induction coil through said lower opening, including a crucible pedestal and a cover extending beneath said crucible pedestal for covering said lower opening;

a rotatable and radially movable tray disposed adjacent to said elevator means and having a plurality of crucible recetacle openings for receiving and holding crucibles and radially receiving said crucible pedestal;

a frame disposed adjacent to said elevator means;

a table movably mounted on said frame for horizontal movement toward and away from said elevator means;

a spindle rotatably mounted on said table and upon which said tray is received, such that said tray is disposed horizontally and rotates with said spindle;

screw drive means mounted on said frame and connected to said table for horizontally moving said table toward and away from said elevator means;

cam drive means mounted on said table and connected to said spindle for rotationally advancing said crucible receptacle openings one receptacle opening at a time; and control means for controlling said screw drive means, said cam drive means, said elevator means and said induction furnace to sequentially and cooperatively raise and lower crucibles to and from said crucible receptacle openings in said tray, raise and lower crucibles to and from the said induction coil and analyze by induction furnace analysis samples in said crucibles when disposed in said induction coil.

8. The automated sample analyzer of claim 7 which further comprises:

weight reading means for detecting weight data of a sample in a crucible;

combustion chemical reading means for detecting combustion chemical data from induction furnace analysis in said induction furnace; and recording and computing means connected to said weight reading means, said combustion chemical reading means, and said control means for receiving data therefrom and recording and computing a compared analysis of this data responsive to said control means such that a compared analysis is recorded for each sample in each crucible sequentially moved to and from said induction coil.

9. The automated sample analyzer of claim 7 wherein said tray is removably mounted on said spindle.

10. The device of claim 7 which further comprises:
an enclosure extending about said elevator means, said tray, said frame, said table, said spindle, said screw drive means and said cam drive means for protecting samples disposed on said tray; and
gas supply means connected to said enclosure for filling said enclosure with a gas not reactive with samples disposed on said tray.

11. The automated sample analyzer of claim 7 wherein said tray includes an indication means for indicating the location of a last crucible in a series of crucibles disposed in said crucible receptacle openings and wherein said control means is connected to said indication means such that said control means halts the operation of said sample analyzer responsive to said indication means.

* * * * *